United States Patent [19]
Griss et al.

[11] Patent Number: 4,923,473
[45] Date of Patent: May 8, 1990

[54] HEMISPHERICAL ACETABULUM

[75] Inventors: Peter Griss, Marburg, Fed. Rep. of Germany; Rudolf Koch, Berlingen, Switzerland

[73] Assignee: Sulzer Brothers Limited, Winterthur, Switzerland

[21] Appl. No.: 308,428

[22] Filed: Feb. 9, 1989

[30] Foreign Application Priority Data

Mar. 1, 1988 [CH] Switzerland ............... 00770/88

[51] Int. Cl.⁵ .................................. A61F 2/34
[52] U.S. Cl. ..................................... 623/22
[58] Field of Search .................. 623/18, 20, 22, 23

[56] References Cited

U.S. PATENT DOCUMENTS

| | | | |
|---|---|---|---|
| 3,543,749 | 12/1970 | Grove | 623/22 |
| 3,641,590 | 2/1972 | Michele | 623/22 |
| 3,740,769 | 6/1973 | Haboush | 623/22 |
| 3,896,504 | 7/1975 | Fischer | 623/22 |

FOREIGN PATENT DOCUMENTS

| | | | |
|---|---|---|---|
| 0149425 | 7/1985 | European Pat. Off. | 623/22 |
| 2225924 | 11/1974 | France | 623/22 |
| 2137098 | 10/1984 | United Kingdom | 623/18 |
| 02535 | 6/1985 | World Int. Prop. O. | 623/22 |

*Primary Examiner*—David J. Isabella
*Attorney, Agent, or Firm*—Kenyon & Kenyon

[57] ABSTRACT

The hemispherical acetabulum has a pin which projects from the cup of the acetabulum on an angle of 45° relative to the polar axis. A sleeve which closes over the pin is rotatably mounted on the pin to facilitate twisting of the cup into a correct position when implanted in a pelvis. The sleeve is made of metal to preclude direct contact between the pin which may be made of plastic and the pelvis bone tissue.

6 Claims, 1 Drawing Sheet

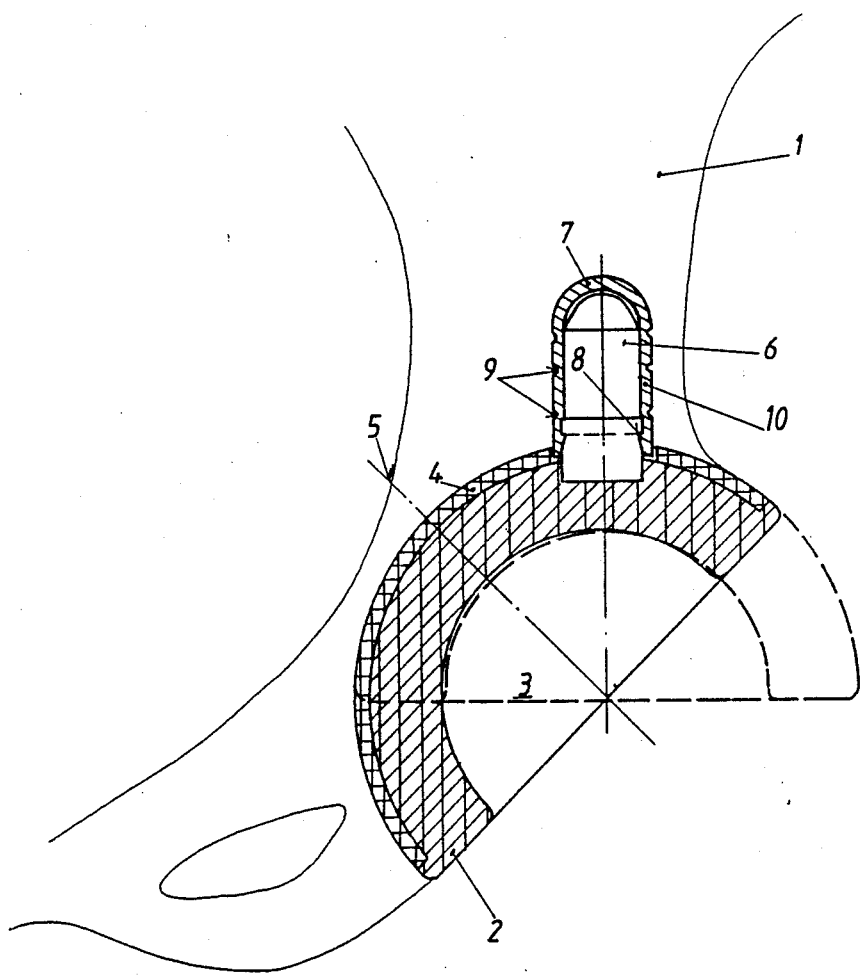

HEMISPHERICAL ACETABULUM

This invention relates to a hemispherical acetabulum. More particularly, this invention relates to a hemispherical acetabulum having a fixing pin which projects from the outside surface of the acetabulum.

Heretofore, various types of acetabulum constructions have been known for implantation in a pelvis. For example, European Patent Application No. 0211619 describes an acetabulum having a fixing pin which projects from the outside surface of the acetabulum at an angle of 45°. Recently, an implantation technique has been developed for acetabula of this kind in which the operating surgeon first prepares the pelvis operatively and then introduces the pin of the acetabulum into a bore in the pelvis prepared therefor with the remainder of the acetabulum being offset, for example about 180°. Thereafter, the surgeon twists the acetabulum into the correct position such that the pin serves as a rotation axis enabling the hemispherical acetabulum to be "guided" into its correct position.

It is an object of this invention to facilitate and simplify the procedure for implanting a hemispherical acetabulum having an angularly disposed fixing pin thereof.

Briefly, the invention provides a hemispherical acetabulum comprising a hemispherical cup having a cavity for receiving a femoral head, a fixing pin secured to the cup and projecting from the cup at an angle of 45° relative to an equatorial plane of the cup (or the polar axis of the cup) and a sleeve which is rotatably mounted on the pin and which has a closed end enclosing the pin.

The sleeve and pin form a cylindrical journal bearing to facilitate twisting of the cup into position into a pelvis. In this respect, the sleeve forms a bearing in which the twisting movement "runs" much more easily than in a bore in a bone. As such, the sleeve facilitates accurate maintenance of a predetermined angle of twisting.

The fixing pin may be made of plastic. In this case, the sleeve which is usually made of metal also provides a screening effect to preclude direct contact between the plastic pin and the bone tissue.

These and other objects and advantages of the invention will become more apparent from the following detailed description taken in conjunction with the accompanying drawing wherein:

The FIGURE diagrammatically illustrates a cross-sectional view taken in a meridian plane which contains the pin axis of an acetabulum constructed in accordance with the invention.

Referring to the drawing, the hemispherical acetabulum is constructed to be inserted into a pelvis 1 and comprises a plastic cup of hemispherical shape having a cavity 3 for receiving a femoral head (not shown). In addition, the acetabulum has a multilayer wire mesh 4 covering the cup 2 on the outer surface with at least one layer embedded in the cup in known fashion.

The acetabulum also has a plastic fixing pin 6 secured to the cup 2 and projecting through the wire mesh 4 on an angle of 45° relative to the polar axis 5 of the cup 2. In similar fashion, the pin 6 is also disposed at an of angle 45° relative to an equitorial plane of the cup 2. The pin 6 may be secured to the cup, for example by friction welding and may also be made of metal.

The acetabulum also has a metal sleeve 7 rotatably mounted on the pin 6 with a closed end enclosing the pin 6. The sleeve 7 is mounted on the pin 6 in spaced relation to the cup 2 and to the wire mesh 4 so as to be freely rotatable on the pin 6. The connection between the pin 6 and the sleeve 7 is by means of a snap fastening 8 in which the pin 6 engages when pushed into the sleeve 7. The generated surfaces of the pin 6 and the sleeve 7 form a cylindrical journal bearing 10.

As indicated, the outer surface of the sleeve 7 is structured, for example with grooves 9, for fixing in the pelvis 1.

In order to use the acetabulum, the surgeon prepares the pelvis 1 to receive the acetabulum. During this time, a bore is made in the pelvis for receiving the sleeve 7. Thereafter, the acetabulum is inserted into the pelvis 1 such that the sleeve 7 is seated in the prepared bore. The acetabulum may then be twisted about the axis of the sleeve 7 and, thus, the pin 6 so as to be brought into proper position.

The invention thus provides an acetabulum having a fixing pin which projects from the outside surface of the acetabulum which can be implanted in a facile and simple manner. In addition, the invention provides an acetabulum which can be twisted into position in a prepared pelvis without causing damage to the fixing pin, particularly, when made of plastic and without causing a reaming action in the bore prepared for reception of the sleeve.

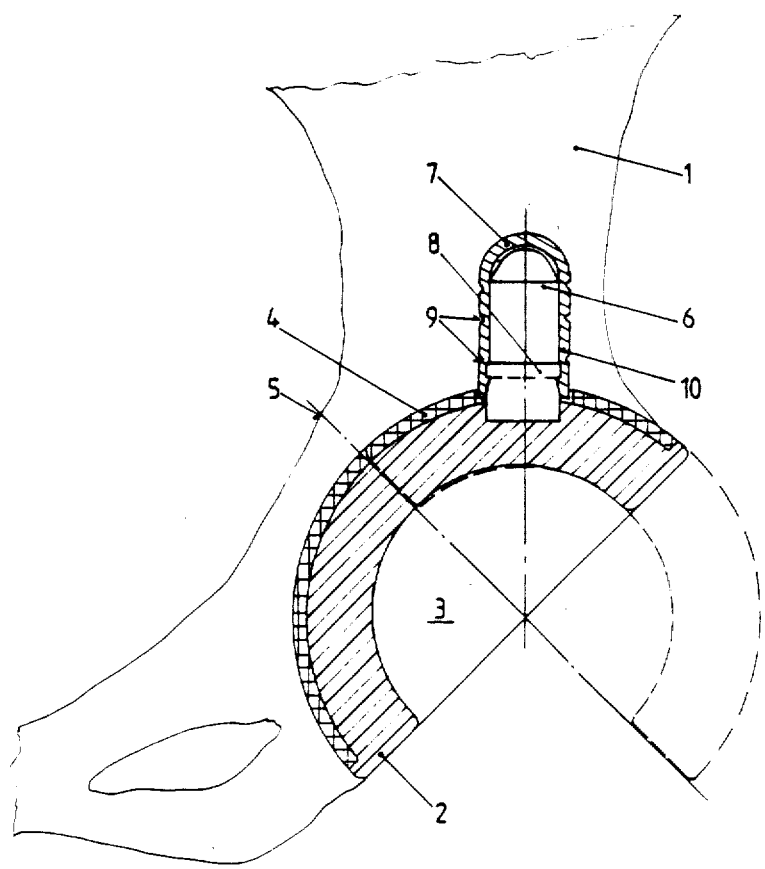

What is claimed

1. A hemispherical acetabulum comprising
   a hemispherical cup having a cavity for receiving a femoral head;
   a fixing pin secured to said cup and projecting from said cup at an angle of 45° relative to an equatorial plane of said cup; and
   a sleeve freely rotatably mounted on said pin and having a closed end enclosing said pin to facilitate twisting of said cup into position in a pelvis.

2. A hemispherical acetabulum as set forth in claim 1 which further comprises means for snap fastening said sleeve on said pin.

3. A hemispherical acetabulum comprising
   a plastic cup having a cavity for receiving a femoral head;
   a pin fixed in said cup and projecting therefrom on an angle of 45° relative to an equatorial plane of said cup; and
   a sleeve freely rotatably mounted on said pin and having a closed end enclosing said pin to facilitate twisting of said cup into position in a pelvis.

4. A hemispherical acetabulum as set forth in claim 4 wherein said sleeve is spaced from said cup.

5. A hemispherical acetabulum as set forth in claim 4 wherein said pin is made of plastic and said sleeve is made of metal.

6. A hemispherical acetabulum comprising
   a plastic cup having a cavity for receiving a femoral head;
   a multilayer wire mesh covering said cup and having at least one layer embedded in said cup;
   a plastic pin fixed in said cup and projecting through said wire mesh on an angle of 45° relative to a polar axis of said cup; and
   a metal sleeve rotatably mounted on said pin in spaced relation to said cup and said wire mesh, said sleeve having a closed end enclosing said pin.

* * * * *

UNITED STATES PATENT AND TRADEMARK OFFICE
CERTIFICATE OF CORRECTION

PATENT NO. : 4,923,473

DATED : May 8, 1990

INVENTOR(S) : PETER GRISS, et al

It is certified that error appears in the above-identified patent and that said Letters Patent is hereby corrected as shown below:

The title page should be deleted to appear as per attached title page.

Signed and Sealed this

Twenty-fourth Day of December, 1991

*Attest:*

HARRY F. MANBECK, JR.

*Attesting Officer*  *Commissioner of Patents and Trademarks*

United States Patent [19]
Griss et al.

[11] Patent Number: 4,923,473
[45] Date of Patent: May 8, 1990

[54] HEMISPHERICAL ACETABULUM

[75] Inventors: Peter Griss, Marburg, Fed. Rep. of Germany; Rudolf Koch, Berlingen, Switzerland

[73] Assignee: Sulzer Brothers Limited, Winterthur, Switzerland

[21] Appl. No.: 308,428

[22] Filed: Feb. 9, 1989

[30] Foreign Application Priority Data

Mar. 1, 1988 [CH] Switzerland ............ 00770/88

[51] Int. Cl.$^5$ ............................................. A61F 2/34
[52] U.S. Cl. ............................................. 623/22
[58] Field of Search .................. 623/18, 20, 22, 23

[56] References Cited

U.S. PATENT DOCUMENTS

| | | | |
|---|---|---|---|
| 3,543,749 | 12/1970 | Grove | 623/22 |
| 3,641,590 | 2/1972 | Michele | 623/22 |
| 3,740,769 | 6/1973 | Haboush | 623/22 |
| 3,896,504 | 7/1975 | Fischer | 623/22 |

FOREIGN PATENT DOCUMENTS

| | | | |
|---|---|---|---|
| 0149425 | 7/1985 | European Pat. Off. | 623/22 |
| 2225924 | 11/1974 | France | 623/22 |
| 2137098 | 10/1984 | United Kingdom | 623/18 |
| 02535 | 6/1985 | World Int. Prop. O. | 623/22 |

Primary Examiner—David J. Isabella
Attorney, Agent, or Firm—Kenyon & Kenyon

[57] ABSTRACT

The hemispherical acetabulum has a pin which projects from the cup of the acetabulum on an angle of 45° relative to the polar axis. A sleeve which closes over the pin is rotatably mounted on the pin to facilitate twisting of the cup into a correct position when implanted in a pelvis. The sleeve is made of metal to preclude direct contact between the pin which may be made of plastic and the pelvis bone tissue.

6 Claims, 1 Drawing Sheet

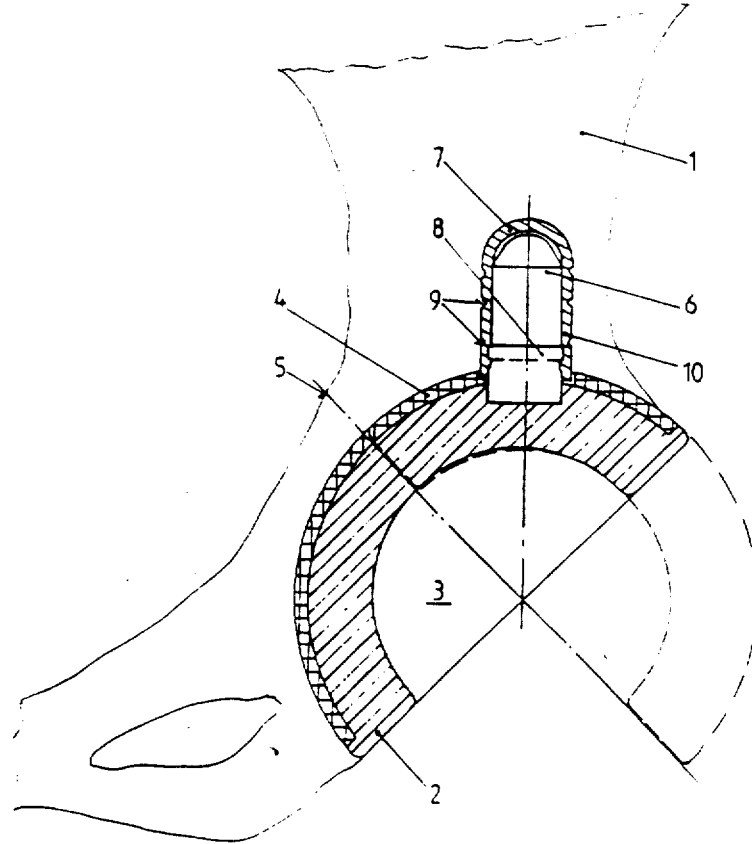

UNITED STATES PATENT AND TRADEMARK OFFICE
CERTIFICATE OF CORRECTION

PATENT NO. : 4,923,473

DATED : May 8, 1990

INVENTOR(S) : PETER GRISS, et al

It is certified that error appears in the above-identified patent and that said Letters Patent is hereby corrected as shown below:

SUBSTITUTE THE FOLLOWING FIGURE FOR THE FIGURE OF THE PATENT